United States Patent [19]

Cianciavicchia et al.

[11] Patent Number: 4,673,927
[45] Date of Patent: Jun. 16, 1987

[54] APPARATUS FOR DETECTING AND CONTROLLING THE LEVEL OF A GASEOUS FLUID

[75] Inventors: Domenico Cianciavicchia, Teramo; Stefano Franceschini, Moglia, both of Italy

[73] Assignee: Hospal A.G., Basle, Switzerland

[21] Appl. No.: 791,487

[22] Filed: Oct. 25, 1985

[30] Foreign Application Priority Data

Oct. 31, 1984 [IT] Italy .................... 68085 A/84

[51] Int. Cl.4 .................................... G08B 21/00
[52] U.S. Cl. ............................. 340/621; 73/19; 73/61 R; 128/660; 128/DIG. 13; 367/908; 604/65
[58] Field of Search ............... 340/605, 606, 608, 609, 340/632, 621; 73/19, 61 R, 290 V; 128/661, 663, 660, DIG. 13; 604/65, 66, 67; 367/908

[56] References Cited

U.S. PATENT DOCUMENTS

| 3,648,694 | 3/1972 | Mogos et al. | 128/DIG. 13 X |
| 3,791,200 | 2/1974 | Hayre | 73/61 R X |
| 3,935,876 | 2/1976 | Massie et al. | 340/603 X |
| 3,974,681 | 8/1976 | Namery | 128/DIG. 13 X |
| 4,068,521 | 1/1978 | Cosentino et al. | 73/19 |
| 4,112,735 | 9/1978 | McKnight | 73/19 |
| 4,418,565 | 12/1983 | St. John | 73/19 |
| 4,481,827 | 11/1984 | Bilstad et al. | 604/65 X |
| 4,487,601 | 12/1984 | Lindemann | 604/67 X |
| 4,501,531 | 2/1985 | Bilstad et al. | 604/67 X |
| 4,607,520 | 8/1986 | Dam | 73/19 |

Primary Examiner—James L. Rowland
Assistant Examiner—Daniel Myer
Attorney, Agent, or Firm—Gerald D. Sharkin; Robert S. Honor; Walter F. Jewell

[57] ABSTRACT

An apparatus for detecting and controlling the presence of a gaseous fluid in relation to a predetermined level of liquid in a vessel, being of the ultrasonic type and comprising a pair of piezoelectric transducers, namely a transmitter and a receiver, capable of being disposed on opposite walls of the vessel. An oscillator provides an electric ultrasonic frequency signal to the transmitter transducer and a comparator compares the electric signal supplied by the receiver transducer with a reference signal for triggering an alarm signal when the disparity between the signals being compared exceeds a predetermined value.

The apparatus moreover comprises processing means which periodically interrupt the electric signal sent to the transmitter transducer and which check the presence of an alarm at the output of the above mentioned comparator.

19 Claims, 1 Drawing Figure

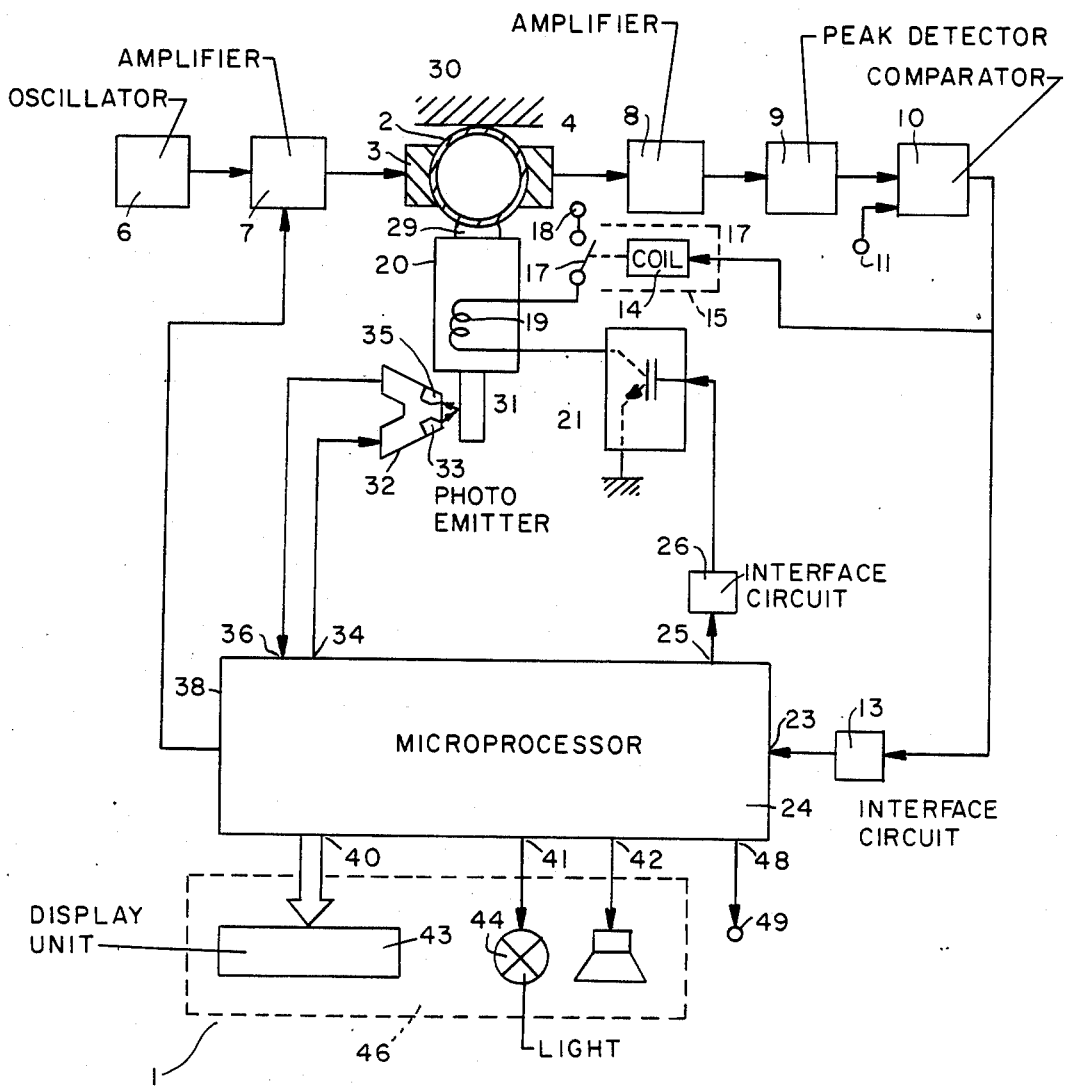

APPARATUS FOR DETECTING AND CONTROLLING THE LEVEL OF A GASEOUS FLUID

FIELD OF THE INVENTION

The present invention concerns an apparatus for detecting and controlling the presence of a gaseous fluid in relation to a predetermined liquid level in a vessel.

More particularly, this invention concerns an apparatus of the ultrasonic type essentially comprising a pair of piezoelectric transmitter and receiver transducers, capable of being placed on opposite walls of the vessel; and an oscillator supplying an electric ultrasonic frequency signal to the transmitter transducer and a comparator which compares the electric signal provided by the receiver transducer with a reference signal, and capable of setting off an alarm signal when the disparity between the signals to be compared exceeds a predetermined value.

PRIOR ART

The known apparatuses of the type described above are advantageously used for very different applications. For example, such apparatuses may be used for detecting the presence of bubbles or of foam inside a vessel containing blood and incorporated in an extracorporeal blood circuit. It is not necessary to stress how important it is to satisfy oneself of the correct functioning in the case of such an application, to make it possible to prevent a return of blood which carries air and could produce an embolism.

The known apparatuses mentioned above have the serious drawback that they cannot inform the operator or the patient of any failures to which they may be subjected. As one instance, a fault in the comparator which compares the electric signal supplied to the receiver transducer with a reference signal could for example block such a comparator and inhibit the triggering of the alarm.

OBJECT OF THE INVENTION

It is an object of the present invention to provide an apparatus capable of detecting the presence of a gaseous fluid in a liquid contained in a vessel and which would make it possible to avoid the drawbacks of the known apparatuses of the type mentioned above.

SUMMARY OF THE INVENTION

The present invention provides an apparatus for detecting and controlling the presence of a gaseous fluid in relation to a predetermined level of liquid in a vessel and which comprises: a pair of electro-acoustic transducers, namely a transmitter and receiver, capable of being placed in diametrically opposite positions in relation to the said vessel in face-to-face contact therewith and in accordance with the said predetermined level; the said receiver transducer being capable of cooperating with the said transmitter transducer and of emitting an electric signal whose amplitude depends on the amplitude of an acoustic signal supplied by the said transmitter transducer and on the quantity of gaseous fluid between the said transducers; means for supplying an ultrasonic frequency electric signal to the said transmitter transducer; means for comparing the electric signal supplied by the said receiver transducer with an electric reference signal, the said comparison means being capable of setting off an alarm signal each time the said electric signal supplied by the said transducer diverges from a predetermined value of the said reference signal; and processing means connected to the supply means and the comparison means, capable of either periodically interrupting the sending of the electric signal to the said transmitter transducer during a predetermined period of time, and of accordingly checking the presence of the said alarm signal, or of receiving the said alarm signal produced by the presence of the said gaseous fluid in the said vessel between the said transmitter and receiver transducers and, in each of the two cases, of controlling the actuating means and/or the signalling means.

BRIEF DESCRIPTION OF THE DRAWING

To render the present invention more readily understood there will be described a preferred embodiment, by way of a non-restrictive example and with reference to the attached drawing in which the sole FIGURE represents the circuit diagram of a detector and control apparatus in accordance with the present invention.

DESCRIPTION OF THE PREFERRED EMBODIMENT

This drawing shows an apparatus for the detecting and control of the presence of a gaseous fluid in accordance with a predetermined level of a liquid in a vessel 2. More particularly, but not exclusively, the liquid contained in vessel 2 can be blood, in which case, the vessel 2 would have the role of a bubble clearance chamber disposed in an extracorporeal blood circuit.

The apparatus 1 essentially comprises a pair of piezoelectric transducers, namely a transmitter 3 and a receiver 4 capable of being placed face to face and diametrically opposed relative to the external surfaces of the vessel 2 and in register with a predetermined level at which it is desired to be able to detect the presence of a gaseous fluid, such as micro-bubbles or foam.

The transmitter transducer 3 is electrically energized by an oscillator 6 capable of providing an electric ultrasonic frequency signal, for example 2MhZ, which oscillator is followed by an amplifier 7, advantageously a differential amplifier.

The receiver transducer 4 is made from a material identical with that of the transmitter transducer 3—for example with a piezoelectric ceramic material—and is connected to the input of an amplifier 8, constituting a band filter, whose output is connected to the input of a peak detector circuit 9 of a type known per se. The output of the peak detector is connected to the first input of a threshold comparator 10 whose second input receives a signal from terminal 11 connected, in a manner not shown, to a reference signal generator.

The output of the comparator 10 is connected both to a circuit interface 13, and to the power input of a coil 14 for energizing a relay 15. The relay 15 has a switch 17 of the normally-open type, activated by the coil 14, and whose first terminal is connected to a terminal 18 which is in turn connected, in a way not shown, to a direct current supply source.

The second terminal of the switch 17 is connected to the first terminal of the coil 19 of an electro-magnet 20. The second terminal of the coil 19 is connected to earth via an electronic or solid state switch 21, made in an appropriate manner by one or several transistors.

The output of the interface circuit 13 is connected to input 23 of a processor unit 24 for example incorporating a microprocessor.

An output 25 of the processor unit is connected via an interface circuit 26 to an input controlling the electronic switch 21 whose function is, in cooperation with the switch 17, to energize the coil 19 of electromagnet 20 by connecting its terminals to earth and to the above mentioned D.C. power source, respectively.

The function of the electromagnet 20 is to block the flow of liquid flowing in vessel 2 by the displacement of its core 29 toward vessel 2 and against a counter pressure element 30 which is fixed in position in relation to the body of the electro-magnet 20 in a position on the opposite side of the vessel 2.

The core 29 has, on the end remote from the vessel 2, an appendage 31 whose axial position is monitored by an optical reflection type transducer 32 of a known type. Such a transducer essentially comprises a photo-emitter element 33 capable of receiving an electric signal from an output 34 of the processor unit 24 and a photo-receiver element 35 capable of receiving an optical signal emitted by the photo-emitter element 33 and reflected by means of the appendage 31, and capable of sending an electric signal to input 36 of the processor unit 24.

The processor unit 24 has an output 38 which periodically emits an electric signal which, forwarded to a control input of the differential amplifier 7, blocks the transmission of the signal generated by the oscillator 6 towards the transmitter transducer 3. By way of example, the signal emitted by output 38 can have a period of 200 milliseconds and a duration of a few milliseconds. Moreover, in the case where the amplifier 7 has a differential type stage, such a signal at the output 38 may be used for inhibiting a current generating circuit located in the above mentioned differential stage so as to inhibit the passing of any electric signal between the input and output of the amplifier.

The processor unit 24 has moreover a plurality of outputs 40, 41, 42, connected respectively to (a) a display unit 43 (b) a warning light 44 and (c) a sound alarm 45 each of which constitutes the signalling means 46 for a particular operating mode of the apparatus 1.

The processor unit 24 has moreover an output 48 connected to a terminal 49 to which there may be connected a control device actuated by the processor unit 24 in predetermined conditions of use. By way of example, such a control device can comprise a pump capable of causing the liquid to circulate inside vessel 2 and which could be normally stopped in predetermined alarm conditions.

Apparatus 1 functions as follows: the transmitter transducer 3 and receiver transducer 4 are diametrically opposite in relation to vessel 2 and care is taken not to allow air to penetrate between the opposite contact surfaces. Under normal operating conditions, core 29 adopts the position illustrated in the FIGURE, which corresponds to the energisation of the coil 19 thanks to the closing of both the switch 17 and of the electronic switch 21.

In the conditions described above, the processor unit 24 generates, for example every 200 milliseconds, the above mentioned interruption signal generated at output 38 which, via the intermediary of amplifier 7 entails interruption of transmission of the signal energising the transmitter transducer 3 during an extremely short period, for example, some milliseconds.

It is obvious that during these short periods, the receiver transducer 4 does not receive any acoustic signal and hence does not emit any electric signal to be detected by way of the amplifier 8, the peak detector circuit 9, and the comparator 10, this signifying an anomaly which is in all respects equivalent, from an operational point of view, to the presence of a gaseous fluid between the transducers 3 and 4.

The signal emitted at the output of comparator 10 therefore arrives at both the relay 15 and the interface circuit 13 at the input 23 of the processor unit 24. By choosing the relay 15 and the electromagnet 20 in such a way that the reaction time should be distinctly greater than that of the brief interruption of the electric signal actuated by the processor unit 24, the electro-magnet 20 is thus prevented from being displaced to shut off the liquid flow.

Moreover, processor unit 24 satisfies itself that, to every loss in transmission of the signal coming from the transmitter transducer 3, there does effectively correspond the generation of an alarm signal so as to ensure that any fault, concerning for instance the amplifier 8, the peak detector 9 or the comparator 10, cannot fail to be detected as a failure of the electric signal at the output of the receiver transducer.

In the operating conditions mentioned above, the processor unit 24 also controls the correct operation of the optical reflection transducer 32, for instance by periodically interrupting the signal energising the photoemitter element 33 and by checking that to the input 36 there does effectively correspond a failure of the electric signal generated by the corresponding photo-receiver element 35. If no anomaly occurs, the processor unit 24 periodically repeats the operations controlling the circuit so as to control constantly the functioning of the essential circuits of apparatus 1.

If any anomaly were to occur, as a result of which the output of the comparator circuit would not trigger an alarm signal at the moment the energising signal for the transmitter transducer disappears, the processor unit 24 would ensure, by means of the interface circuit 26, the opening of the electronic switch 21 which would interrupt the energising of the coil 19. This would entail the immediate displacement of the core 29 of the electromagnet 20 and as a result, the closing of the tubing in which the liquid of vessel 2 circulates. The monitoring of the effective displacement of core 29 is effected by the optical transducer 32 in that the photo-receiver element 35 will not receive any signal once the core 29 has been displaced along with the pin 31. As a result, the processor unit triggers either the illumination of the warning lamp 44 or the energisation of the acoustic alarm 45.

Moreover, the possible lack of displacement of core 29 would be immediately discovered by the optical reflection transducer 32 and signalled to the operator for instance by causing a predetermined code to appear on the display unit 43.

A real presence of a gaseous fluid between transducers 3 and 4 is manifested by a diminution in amplitude of the electric signal coming from the receiver transducer 4 and thus, by means of the comparator circuit 10, the triggering of a continuous alarm which in this case comprises either the opening of switch 21 by the processor unit 24, or the opening of contact 17 of the relay 15 thanks to the energisation of the corresponding coil 14.

Obviously even in such a case, the sound alarm 45 and the illumination of the lamp 44 can be triggered and also, if it has been suitably prepared, the presentation of a code signalling the faults on the display unit 43. In view of what has been stated above, the processor unit 24 could also send a signal to the terminal 49 and for instance disenable a pump which normally operates the flow of the liquid in vessel 2.

An examination of the characteristics of the apparatus in accordance with the present invention reveals the advantages which it derives. It is above all capable of verifying the effectiveness of the transmission chain comprising the oscillator 6, the amplifier 7, the transducers 3 and 4, the amplifier 8, the detector 9 and the comparator 10 with a frequent repetition of monitoring (for instance 5 times per second).

In this way, it is also possible to check the correct positioning of the transducers 3 and 4 relative to the vessel 2. An undesired introduction of air between the contiguous contact surfaces would be detected like the presence of air inside the liquid contained in vessel 2 and signalled as an abnormal situation.

The intervention of the electro-magnet in the case of detection of a gaseous fluid in the form of bubbles, foam or in a diminution in the level of liquid in the vessel 2 below a predetermined limit, is effected in two independent ways; that is to say, by the relay 15 and by the processor unit 24 and this contributes to increasing the safety of apparatus 1 even if one of the two above mentioned means were to become defective. Moreover, the periodic checking of the effectiveness of the optical reflection transducer 32 contributes towards increasing the safety level of apparatus 1.

It is obvious that variants or modifications can be applied to the mode of embodiment described for apparatus 1 without thereby departing from the scope of the present invention.

We claim:

1. In an apparatus for the detection and control of presence of a gaseous fluid in relation to a predetermined level of liquid in a vessel, the apparatus comprising:
   (a) transmitter electro-acoustic transducer means and receiver electro-acoustic transducer means, capable of being placed in face-to-face contact with the vessel in diametrically opposite positions in relation thereto at the predetermined level; the receiver transducer being capable of cooperating with the transmitter transducer means and of emitting an electric signal whose amplitude depends on the amplitude of an acoustic signal provided by the transmitter transducer and on the quantity of gaseous fluid in the vessel between the transducers;
   (b) signal generating means for providing an electric ultrasonic frequency signal to the transmitter transducer means, comprising an oscillator, and an amplifier connected downline from the oscillator, the amplifier having its own current generator controlled by a periodic signal coming from the output of a microprocessor processing means, and capable of periodically activating and deactivating the current generator;
   (c) signalling means for signalling an alarm condition;
   (d) means for comparing the electric signal provided by the receiver transducer means with an electric reference signal, said comparing means being capable of triggering an alarm signal to the signalling means each time the electric signal provided by the receiver transducer means diverges from a predetermined value of the reference signal: the improvement comprising:
   (e) actuating means for modifying the level of the liquid in the vessel in response to an alarm condition;
   (f) said microprocessor processing means connected to the signal generating means and to the comparing means, capable one of (fa) periodically interrupting the electric signal to the transmitter transducer for a predetermined period of time and of checking accordingly the presence of the alarm signal, and (fb) receiving the alarm signal produced by the presence of the gaseous fluid in the vessel between the transmitter transducer means and the receiver transducer means and, in each one of these two cases (fa and fb), of controlling at least one of the two actuating means and the signalling means.

2. Apparatus according to claim 1 wherein the amplifier is of the differential type.

3. Apparatus according to claim 1 and including an amplifier and a peak detector circuit between the receiver transducer means and input of said comparison means.

4. Apparatus according to claim 3 wherein said amplifier is of the limited filter type.

5. Apparatus according to claim 1 including tubing in which the liquid in said vessel circulates, and wherein said actuating means comprise an electro-magnet provided with a movable core capable of actuating the closing of said tubing.

6. Apparatus according to claim 5 wherein said tubing includes an elastic deformable wall, and wherein said movable core is capable of axial displacement by elastically deforming the walls until said tubing is closed.

7. Apparatus according to claim 5 including an energizing coil for said electromagnet, an electric switch adapted to be closed for energizing said coil and a control element controlled by the said comparison means, wherein said electric switch forms part of said control element.

8. Apparatus according to claim 7 wherein the control element is a relay and said comparison means are connected to the coil of said relay.

9. Apparatus according to claim 5, including a switch controlled by said processor means, and wherein said coil energizing the said electro-magnet is supplied via said switch.

10. Apparatus according to claim 9, wherein said switch is of the electronic type.

11. Apparatus according to claim 10, wherein said electronic switch comprises at least one transistor.

12. Apparatus according to claim 5, wherein said electro magnet has a mechanical response time which is substantially greater than the said period of interruption of said electric signal supplied to the said transmitter transducer means.

13. Apparatus according to claim 5, and further including control means capable of checking the axial displacement of said movable core of the electromagnet.

14. Apparatus according to claim 13, wherein said control means are placed near one end of said core which is remote from the part of said core actuating the closing of said tubing.

15. Apparatus according to claim 13, wherein said control means comprise an optical reflection transducer constituted by a photo-emitter element and by a photoreceiver element in association with a movable reflector.

16. Apparatus according to claim 15, wherein said processing means has an input and an output, and wherein said photo-emitter and photoreceiver elements are connected to said output and to said input, respectively, of said processing means.

17. Apparatus according to claim 16, wherein said processing means are capable of providing, via said output, an intermittent energizing signal for said photo-emitter element and capable of checking at said input that the corresponding electric signal has been received by the photoreceiver element.

18. Apparatus according to claim 1, wherein said signalling means comprise at least one of the optical and acoustic type.

19. Apparatus according to claim 18, wherein said signalling means are of the optical type and comprise a display unit for codified information.

* * * * *